(12) United States Patent
Nielsen

(10) Patent No.: US 8,815,361 B2
(45) Date of Patent: Aug. 26, 2014

(54) SILICONE URISHEATH WITH INTEGRATED ADHESIVE

(75) Inventor: Henrik Lindenskov Nielsen, Smoerum (DK)

(73) Assignee: Coloplast A/S, Humlebaek (DK)

( * ) Notice: Subject to any disclaimer, the term of this patent is extended or adjusted under 35 U.S.C. 154(b) by 2224 days.

(21) Appl. No.: 11/661,987

(22) PCT Filed: Sep. 5, 2005

(86) PCT No.: PCT/EP2005/054373
§ 371 (c)(1),
(2), (4) Date: Mar. 12, 2008

(87) PCT Pub. No.: WO2006/027349
PCT Pub. Date: Mar. 16, 2006

(65) Prior Publication Data
US 2008/0187693 A1     Aug. 7, 2008

Related U.S. Application Data

(60) Provisional application No. 60/690,892, filed on Jun. 16, 2005.

(30) Foreign Application Priority Data

Sep. 6, 2004   (DK) .................................. 2004 01343

(51) Int. Cl.
*B32B 1/08* (2006.01)
*B05D 3/00* (2006.01)
*A61F 5/44* (2006.01)
*C08J 7/12* (2006.01)

(52) U.S. Cl.
CPC ...................................... *C08J 7/123* (2013.01)

USPC .......................... 428/36.9; 427/2.3; 604/349

(58) Field of Classification Search
CPC ... D06M 10/00; D06M 10/02; D06M 10/025; H01T 19/00
USPC ...................... 427/208.4, 535, 1–2.31, 207.1; 428/34.1; 604/349
See application file for complete search history.

(56) References Cited

U.S. PATENT DOCUMENTS 3,632,386 A  *  1/1972  Hurst ........................... 428/345
4,373,009 A       2/1983  Winn (Continued)

FOREIGN PATENT DOCUMENTS

| EP | 0 606 014 A1 | 7/1994 |
| JP | 11 255926 A | 9/1999 |
| WO | WO8600816 A1 * | 2/1986 |
| WO | WO 98/018852 | 5/1998 |
| WO | WO0014146 A1 * | 3/2000 |
| WO | WO 0014146 A1 * | 3/2000 |

OTHER PUBLICATIONS

Webster, "Recent developments in pressure-sensitive adhesives for medical applications," Int. J. Adhesion and Adhesives, vol. 17, No. 1, 1997.*

(Continued)

*Primary Examiner* — Michele L Jacobson
*Assistant Examiner* — Susan R Dye
(74) *Attorney, Agent, or Firm* — Coloplast Corp., Coloplast A/S; Nick Baumann

(57) ABSTRACT

By using an oxidative process, it is possible to apply an adhesive material to silicone. The process is controlled, allowing selective oxidative treatment to a silicone structure, thus enabling treatment to the inside of a tubular structure.

20 Claims, 3 Drawing Sheets

(56) References Cited

U.S. PATENT DOCUMENTS

| | | | |
|---|---|---|---|
| 4,769,099 A * | 9/1988 | Therriault et al. | 156/230 |
| 4,820,289 A * | 4/1989 | Coury et al. | 604/349 |
| 4,840,270 A * | 6/1989 | Caputo et al. | 206/205 |
| 4,885,049 A * | 12/1989 | Johannesson | 156/289 |
| 5,176,666 A | 1/1993 | Conway et al. | |
| 5,466,424 A | 11/1995 | Kusano et al. | |
| 5,472,544 A | 12/1995 | Fukamachi et al. | |
| 5,538,584 A * | 7/1996 | Metz | 156/294 |
| 5,779,964 A | 7/1998 | Welch et al. | |
| 5,879,757 A | 3/1999 | Gutowski et al. | |
| 6,426,138 B1 | 7/2002 | Narushima et al. | |
| 6,706,320 B2 | 3/2004 | Filippou et al. | |
| 6,780,484 B2 | 8/2004 | Kobe et al. | |
| 2002/0018860 A1 | 2/2002 | Filippou et al. | |
| 2003/0044451 A1 * | 3/2003 | McGhee et al. | 424/443 |

OTHER PUBLICATIONS

Tavakoli, "Adhesive Bonding of Medical and Implantable Devices—A Review of Materials, Processes and Applications," Business Briefing: Medical Device Manufacturing & Technology, 2002.*

Clean Seal, Inc., "Acrylic Based Adhesives," Jul. 1, 2003. Online at http://web.archive.org/web/20030701152902/http://www.cleanseal.com/information-06.htm.*

MedicationLink, "Male External Catheters," Aug. 31, 2003. Online at http://web.archive.org/web/20030831025434/http:/www.medicationlink.com/medicat__/drinage__catheter__/html__DC/latex__male__cath__1.htm.*

* cited by examiner

SILICONE URISHEATH WITH INTEGRATED ADHESIVE

CROSS-REFERENCE TO RELATED APPLICATION

This is a national stage of PCT/EP05/054373 filed Sep. 5, 2005 and published in English, claiming benefit of U.S. provisional application number 60/690,892, filed Jun. 16, 2005.

BACKGROUND OF THE INVENTION

1. Field of Invention

The present invention relates to attaching a pressure sensitive skin adhesive only to the inside of a partly or fully cured silicone raw urisheath or on other cured elastomer or thermoplastic elastomer raw urisheaths by using a total or selective oxidative corona, plasma, flame treatment; or UV, E-beam or gamma-irradiation; or chemical oxidative treatment; or by using a silicone tie-layer.

2. Description of the Prior Art

External urinary catheters are conventionally used in urinary catheter devices for aiding male urinary incontinence and for use in hospitals in connection with treatment and surgery of urethral disorders. Such an external urinary catheter normally comprises a sheath or body portion, such as a tubular body, enclosing the shaft of the penis, and a tip portion that is provided with a comparatively short discharge tube, which via a hose is connected to a urine collection bag that is e.g. fastened to the bed or the leg of the user.

Traditionally, the external urinary catheter is delivered in a rolled-up condition. In this delivery condition, the sheath portion is rolled-up in a number of successive windings to such an extent that the layer of adhesive is entirely accommodated in the windings to allow the urisheath to be packaged and handled without the inner side of the sheath portion adhering to the surroundings. In order to apply the external urinary catheter on a penis, the sheath portion is unrolled slightly until the layer of adhesive on the inner side of the sheath portion is exposed. In this condition, the external urinary catheter is positioned on the penis such that the layer of adhesive is brought into contact with the skin and the remaining part of the sheath portion is subsequently unrolled.

Silicone is considered to have good properties for making urisheaths. The main problem about using it is attaching an adhesive securely to the inside of the urisheath, and at the same time being able to unroll the urisheath easily for the user. It has been considered very difficult to attach an adhesive to a ready-made silicone raw urisheath, because silicone materials inherently are release materials for all other pressure sensitive adhesives than silicone adhesives.

U.S. Pat. No. 5,176,666 describes how to adhere a pressure sensitive adhesive to a dipped silicone urisheath. The adhesion is done by dipping a non-cured silicone urisheath on a dipping mandrel where adhesive has already been applied and stripped to the right length, and then curing the silicone on the mandrel with adhesive. The aforementioned process secures at least a physical binding between the silicone and the adhesive.

U.S. Pat. No. 5,779,964 describes how to adhere a pressure sensitive adhesive on an already cured dipped silicone urisheath. This is done by applying the adhesive to the outside of the urisheath, then cure it, and subsequently applying a surface preparation layer on top, which has a greater affinity for the silicone rubber than the adhesive has. By rolling up the urisheath the surface preparation layer comes in contact with the inside of the silicone urisheath, and thereby the adhesive is transferred to the inside of the urisheath together with the surface preparation layer.

Silicone adhesives will be able to attach to a ready-made silicone raw urisheath, but will give the problem of needing to put a special release layer on the outside of the urisheath in order for the silicone pressure sensitive adhesive not to adhere to the outside of the urisheath in the rolled up position.

With all other commonly used pressure sensitive skin adhesives the cured silicone material will give a release effect for the pressure sensitive adhesive, making the adhesive stick to the skin instead of the urisheath when taking the product off after use. With these adhesives the job is, in popular terms, to make the adhesive stick strongly to one side (the inside) of the silicone urisheaths but not to the other (the outside).

There is a need for an alternative way to attach a commonly used pressure sensitive skin adhesives to a partly or fully cured silicone raw urisheath.

SUMMARY OF THE INVENTION

Surprisingly, it has been found that a variety of pressure sensitive skin adhesives, can be attached to the urisheath after a selective corona or plasma treatment only to one side of a partly or fully cured silicone, while maintaining the release properties on the other side of the silicone. If the release properties are not fully maintained, e.g. due to the thiness of the product, or the physical properties of the silicone and/or adhesive composition, an extra silicone layer is attached to cover the outer encircling band covering the area of the adhesive.

DETAILED DESCRIPTION OF THE PREFERRED EMBODIMENTS

Figure 2:
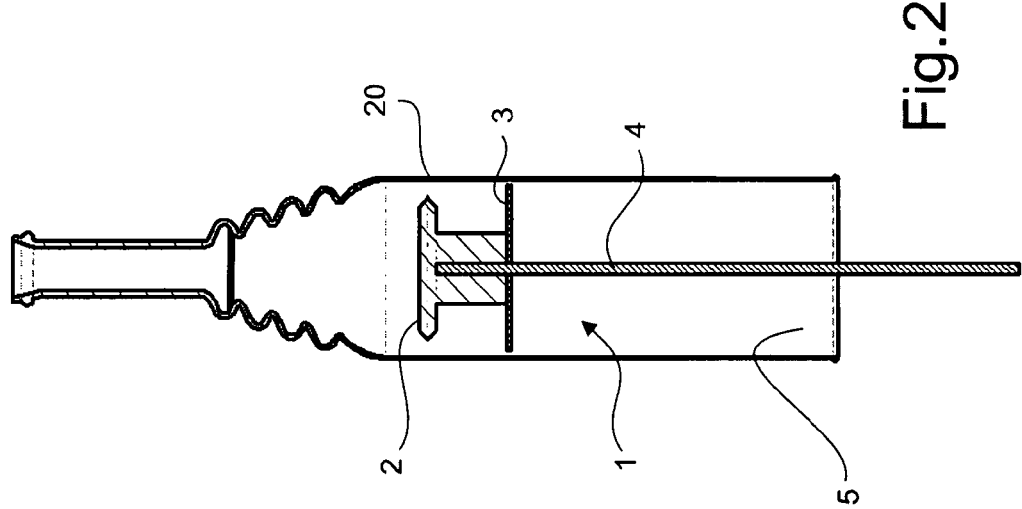
FIG. 2 is a cross-sectional view of the corona electrode inserted into a urisheath.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Thus, the present invention relates to a method for applying an adhesive material to preferentially a silicone elastomer comprising
(a) applying an oxidative process to the elastomer
(b) applying an adhesive to the elastomer.

Using a urisheath as the example, this solution of for example corona treatment of the urisheath enables treatment on the inside without treating the outside. This is done by putting a corona discharge electrode inside the urisheath and moving it along the length of the urisheath in the area that shall be treated, preferentially without touching the surface, while supplying it with sufficient power for treating the inside of the urisheath without having the outside treated. By this corona discharge the low molecular uncured silicone oil present are removed from the inner surface, and polar groups like —OH and —COOH are formed, which can give a rise in the surface tension from below 23 dyn/cm up to 30 to 60 dyn/cm making it possible for a lot of different adhesives, for instance all commonly used pressure sensitive skin adhesive including acrylic PSA's, to wet and thereby physically being attached to the surface. The —OH and —COOH groups formed also makes it possible covalently to bind the adhesive to the silicone if needed. This selective corona treatment can also be done with other possible urisheath materials.

It is often preferred to form the elastomer in a structure, for example a cylinder for the sheath portion or the total urinary catheter (urisheath).

In one embodiment, the elastomer is chemically cross-linked elastomer material like natural rubber latex, nitrile rubber latex, chloroprene rubber latex, SBS rubber latex or other synthetic lattices or in silicone or polyurethane dispersions or emulsions. The Cross linking can be initiated by heat, UV light or E-beam. In another embodiment the elastomer is a thermoplastic elastomer material like styrene elastomer block-copolymers (e.g. SEBS, SBS, SIS, SIBS) or in thermoplastic polyurethane (e.g. Estane), polyetherester (e.g. Hytrel), polyetheramide (e.g. Pebax) or in Polypropylene/EPDM (e.g. Santoprene) polypropylene homo- or co-polymers with controlled tacticity in blocks (Versaflex (Exxon) or Versify (Dow Chemical)). In a preferred embodiment, the elastomer is partial or fully cured silicone.

A silicone material in this context means a polymer material, which contains Silicium in the polymer backbone. Normally, this polymer backbone is mainly consisting of polysiloxan —O—Si—. In many cases the silicone material consist mainly of polydimethylsiloxan (PDMS) but also phenyl and other carbon containing side groups can be used.

Many different curing (vulcanisation) chemistries can be used for silicone. The main categories are addition cured, condensation cured, free radical cured, moisture cured (RTV), UV cured and E-beam cured.

In Addition curing a polysiloxan containing vinyl ($H_2C=CH-$) or other alkenyl groups as end groups or side groups are cured with a crosslinker containing SiH groups. This reaction is normally catalysed by a Platinum or Rhodium containing catalyst. The special systems the SiH groups can also be on the siloxan backbone and then a vinyl or alkenyl containing crosslinker is used.

In Condensation curing a polysiloxan containing OH groups are cured with SiH crosslinker this reaction is normally catalysed by a Stannous containing catalyst and special accelerators coating amine are typically used.

Moisture cured silicones also known as RTV silicones (Room Temperature Vulcanising silicones) are cured by a substitution reaction with H2O and are evolving acetic acid.

In Free Radical curing a polysiloxan containing vinyl ($H_2C=CH-$) or other alkenyl groups as end groups or side groups are cured with a peroxide crosslinker.

In UV curing and E-beam curing a polysiloxan containing acrylate as end groups or side groups are cured with UV or E-beam radiation using photo- or E-beam initiators to initiate and speed up the process. Epoxy silicones can also be used together with a cationic initiator.

For moulding products in a closed mould, Addition cured silicone are preferred as they can be cured only by heat without evolving any gas as for instance H2, H2O or low molecular carbon containing species or are needing any gas like for instance H2O for the curing. In a preferred embodiment of the invention the silicone is mould injected. In a related preferred embodiment, the silicone is a mould injected urisheath.

For silicone release coating many curing types are commonly used. Including addition cured, condensation cured and UV and E-beam cured.

The adhesive material is sitting on the silicone sheath. The binding force keeping those together is increased by the corona treatment disclosed herein. This is because of much increased polarity of the surface that is obtained both by removing volatile silicone oil form the surface and by oxidizing the surface. Apart from the polar forces also some acrylic adhesives can react on curing with the —OH and —COOH groups making a covalent bonding. However, when the sheath is rolled, the adhesive will be in contact with the other side of the silicone sheath. So it is required that the force to remove the adhesive from the other side of the silicone sheath is low. This is secured by selectively avoiding treating of this surface so that it remains unpolar, in its unpolar state. In use, unrolled, the adhesive will be in contact with the skin. The force needed to remove the adhesive from the skin is referred to as the peel value. It is preferred, that the peel value of the adhesive is lower than the binding force to the silicone sheath to avoid adhesive residuals on the skin.

By the above methods described it is possible to use many kind of known skin adhesives, for instance based on acrylics, polyvinylether, polyurethane, polyvinylpyrolidone, SIS, PIB or rubber and getting them securely attached to the silicone raw urisheath. These can be solvent borne, water based, or hot melts, and can eventually be cured by heat, UV-light or E-beam irradiation. Polar pressure sensitive adhesive materials like those based on acrylics, polyether, polyvinylether, polyurethane or polyvinylpyrolidone are preferred. In a preferred embodiment the adhesive material is an acrylic pressure sensitive adhesive.

Styrene elastomer or Polyisobutylene based hotmelt adhesives are other adhesives used very commonly for pressure sensitive skin adhesives. In another embodiment, a solvent borne polyvinylether based adhesive is used.

In one embodiment of the invention, a silicone PSA is used as the skin adhesive, and then using a flouro silicone, or other release material against a silicone PSA, as an integrated release layer on the outside.

In another embodiment a silicone PSA is the skin adhesive and a separate film release-liner is rolled in between the layers in the rolling. This release liner can be made of, e.g., a polyolefin thermoplastic film material.

Typically, the silicone structure is fully cured. However, this is not needed to carry out the oxidative heat process. Consequently, in another embodiment, the silicone structure is partly cured.

One particular advantage of the present invention is the ability to apply adhesive on designated areas only. This is obtained when the oxidative-heat process is applied selectively on selected parts of the product. In the case of a urisheath, the oxidative-heat process is applied selectively on the inside of a silicone external catheter. Thereby, the process is carried out without harming the release properties on the outside of the external catheter.

Silicone is used in a variety of products. For the present purpose, silicone products used as medical products are preferred. That is, for example selected from the group consisting of a catheter, a plaster, a bandage, an external breast prostheses, and an external urinary catheter.

A specific problem that this patent identifies and solves is how to attach a pressure sensitive skin adhesive to a fully cured silicone raw urisheath and at the same time making a fully functional urisheath. Thus, in a preferred embodiment, the silicone structure is an urisheath. It should be understood that by the term fully cured the product is dimensionally stable and suitable for use in for example medical devices. However, there may still be some percentage of uncured silicone oils, typically around 1-5%.

Different oxidative processes can be applied. Such oxidative processes can for example be a chemical treatment of the material, treatment of the material by UV-light, E-beam (also known as β-radiation) or gamma-irradiation or oxidative-heat process.

Many kinds of oxidative-heat processes exist. In one embodiment the oxidative-heat process is a corona treatment. In another embodiment, the oxidative-heat process is a plasma treatment for example using a plasma pen. In yet a third embodiment, the oxidative-heat process is a flame treatment for example by using an oxidative flame.

The particular choice of oxidative treatment depends on the material used, whether silicone or any of the above mentioned other possible materials for the sheath portion of an urinary catheter.

Alternatives of how to apply the adhesive to the silicone structure exist. In one embodiment the adhesive is applied to the oxidative-heat process treated silicone structure by placing said silicone structure on top of an adhesive layer, and shortly thereafter removing said silicone structure. In a special embodiment, the application is by rolling on top of a mandrel with adhesive. In another embodiment, a double-sided tape is applied to a mandrel where-after the silicone structure is rolled over. When rolled-up again, for storage, the adhesive will be placed on the silicone structure.

Yet another solution relates to a method for applying an adhesive material to a cured silicone structure, comprising curing adhesive together by a silicone tie-layer. In this embodiment the binding is secured by a silicone tie-layer.

Other or combined solutions can be to use a special tie-layer. Such a tie-layer can preferentially in itself be a silicone layer. The binding can be a liquid, solvent borne or emulsion silicone, which is based on one or more component and that, is cured by addition or condensation reaction using heat, moisture, UV light, E-beam or other means. The tie-layer can also be an already cured silicone adhesive with PSA properties. The tie-layer can also contain additives like titanates, zirconates or silanes (with or without other functionalities like -acrylic, -amine, -epoxy) in order to secure the binding to either or both of the surfaces of the PSA and the silicone raw urisheath, which it shall bind together. It is preferred that the raw urisheath is made out of a cured silicone material.

In one aspect of the invention, a cleaning step is added, before the attachment of the adhesive. Hereby, traces of uncured low molecular silicone residues are removed. In the example of the urisheath, at least the inside of the silicone structure is cleaned. Methods for cleaning include $CO_2$ washing or $CO_2$ ice blasting.

Corona treatment of silicone elastomer is normally considered to have a short effect because small amounts (1 to 5%) of uncured silicone oils are always left in the product after curing. By evaporating at least some (the low molecular weight part) of the silicone oil from the surface by pre-treating the urisheaths for 5 minutes at 200° C. in an oven tow advantages are obtained:

1. Better result of the corona treatment and a longer period possible between the corona treatment and application of the adhesive.
2. Lower silicone oil content on the outside surface of the urisheath. This means less contamination of the adhesive surface by silicone oil when the urisheath is rolled up.

In this way good results has been obtained after 3 days storage both in rolled an in unrolled position before the application of the urisheath.

It shall be noted that longer evaporation periods (e.g. 1 h at 200° C.) eventually can results in more contamination of the surface, because that higher molecular non-volatile silicone oil will migrate to the surface together with the low molecular volatile silicone oil resulting and a built up of non-volatile silicone oil on the surface at the longer evaporation periods.

It can furthermore be understood that the present invention discloses a tubular body being produced of an elastomer, comprising that, at least an encircling inner band of an oxidized elastomer is provided on the inside of the tubular body, and an outer encircling band of an non-oxidized elastomer is provided on the outside of the tubular body, and that the outer encircling band at least covers the encircling inner band.

By providing an inner encircling band of oxidized elastomer other materials can easily be attached to the tubular body.

In one embodiment the tubular body is a urisheath and adhesive for adhering the urisheath to the skin can advantageously be attached to the encircling inner band.

In one embodiment the encircling inner band is formed of the tubular body. The encircling inner band can for example be formed of the body by oxidizing the inner band. This can for example be done by the oxidative treatments mentioned herein, e.g. corona treatment, plasma treatment or flame treatment.

In another embodiment, the encircling inner band is applied to the tubular body. This can for example be done by applying the layer via a mandrel whereon the oxidized elastomer is provided. The tubular body is then rolled onto the mandrel whereby the oxidized elastomer is transferred onto the inside of the tubular body providing the encircling inner band. Taking advantage of what is known as acrylic lock-up the oxidized elastomer will automatically attach to the tubular body. Acrylic lock-up is a well-known phenomenon for acrylic adhesives on silicone materials (e.g. normally silicone coated release liners).

Normally it is caused by an uncured silicone. A good curing as well as low ratio of SiH groups to $H_2C=CH-$ groups in an Addition cured silicone normally secures that acrylic lock-up will not happen. However in addition to the well described lock-up to SiH groups, also lock-up to $H_2C=CH-$ groups and Si—OH groups has been proposed in the literature (J. L. Keddie: "Evidence from infrared Ellipsometry for Covalent Bonding at a Polymer/Polymer Interface with Relevance to "Lock-Up" in Pressure-Sensitive Adhesive Laminates"). Also acrylic lock-up for a liner that has been E-beam treated in an oxidative environment has been described, whereas E-beam treatment at a low oxygen level (less than 10 ppm) did not cause any lock-up problem (U.S. Pat. No. 6,780,484).

The encircling outer band can advantageously be formed of the tubular body. This can for example be realized when the encircling inner band is provided by for example corona treatment. By only applying corona treatment for a controlled period of time it can be achieved that the encircling inner band is only partly provided in the tubular body. The encircling outer band is thus provided by the non-corona treated part of the tubular body.

Alternatively, by applying the encircling inner band onto the tubular body as described above the encircling outer band can advantageously also be provided by the tubular body.

I another embodiment the encircling outer band is applied to the tubular body. This can for example be done when the inner band is through going in the tubular body. An elastomer, such as a silicone can thereby be applied as the encircling outer band as described above.

By applying an encircling outer band according to any of the methods described above a rolled urisheath having an inner encircling band covered with an adhesive can easily be unrolled when the encircling outer band function as a release layer. A well cured silicone sheath with the right balance of SiH to CH2=CH— groups can secure this, or eventually an extra layer formed of a release silicone coating can be applied, encircling on the outside, in order to get optimal release properties, both initially but also after accelerated or extended ageing.

One advantage of providing an oxidized inner layer is that other materials thereby can bind to the elastomer. Thus an adhesive can for example be provided on the encircling inner band resulting in an elastomer, which will adhere to other surfaces, such as an urisheath that can be adhered to the skin.

Figures

Figure 1:
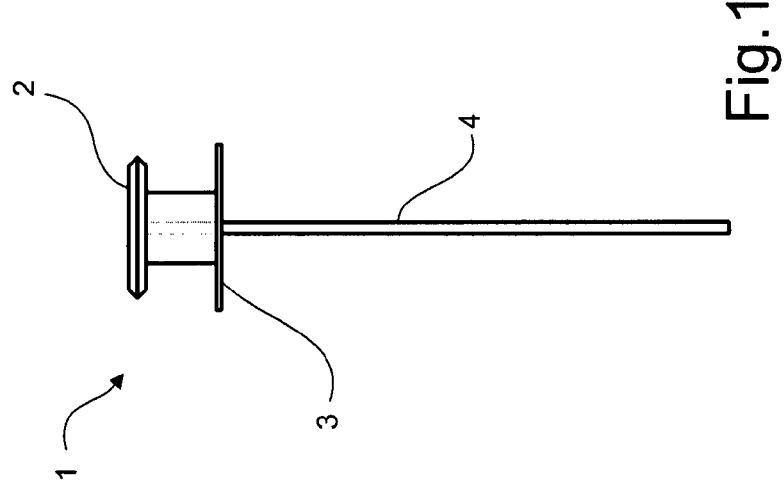
FIG. 1 illustrates a first embodiment of a corona electrode according to the invention.

FIG. 1: Circular Electrode

FIG. 1 illustrates a first embodiment of a corona electrode 1 according to the invention. The electrode is formed of a first circular aluminum electrode head 2, a first PE (polyethylene) disc 3 and a first steel rod 4.

Charging the electrode head creates a corona, for corona treatment. This will basically create a capacitor effect. As the charge grows the air surrounding the electrode head becomes ionized and eventually will become conductive whereby a corona is created. When corona treatment is done in normal oxygen containing air, ozone and free radicals are generated, which subsequently creates chemical reaction with the surface. Also the energy evolved is removing volatile contaminants from the surface. This all together makes it easier to wet the surface with e.g. an adhesive and eventually to make covalent bonding to this.

The PE disc is provided as an insulator. It helps controlling the boundary of the corona so that the corona can be emitted in a controlled band.

FIG. 2: Circular Electrode in Operation

FIG. 2 illustrates, seen in section, the corona electrode 1 inserted into a urisheath 5. During treatment the corona electrode is displaced longitudinal within the urisheath.

Figure 3:
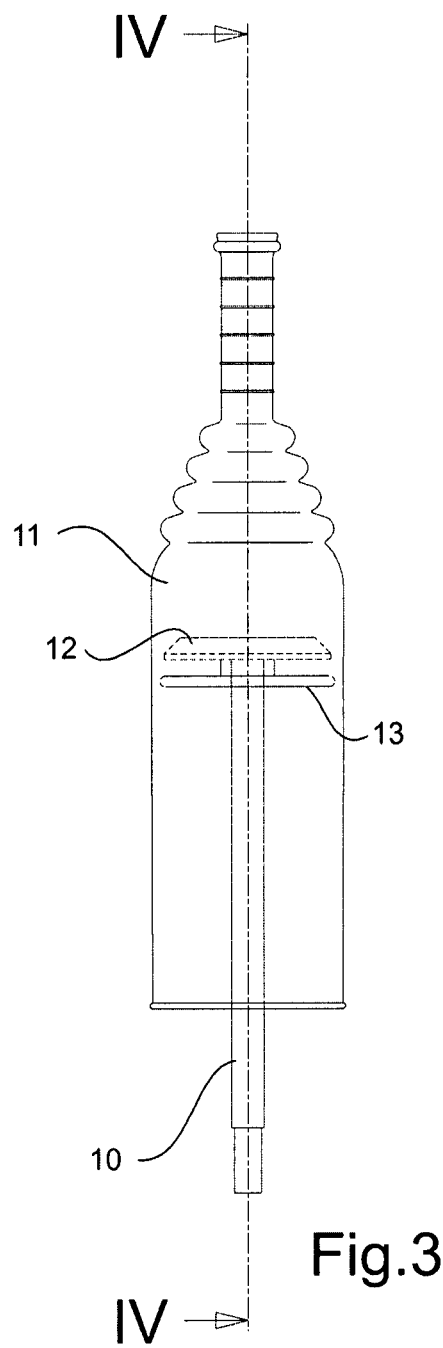
FIG. 3 illustrates a second embodiment of a corona electrode arranged inside a second urisheath.
Figure 4:
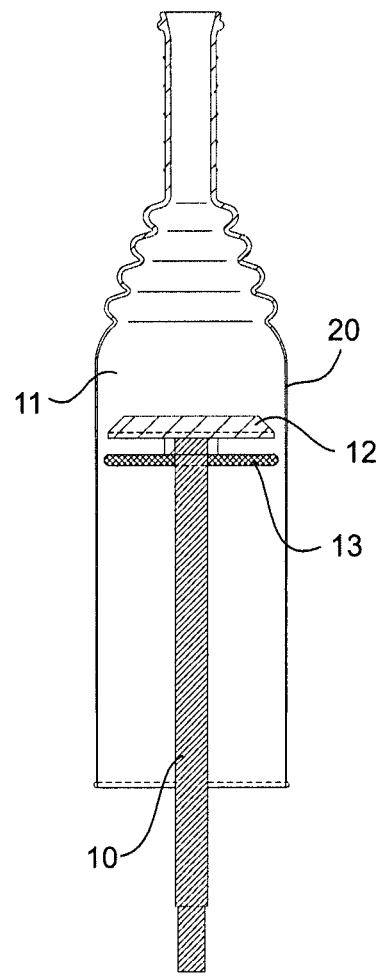
FIG. 4 illustrates the cross section along line IV-IV in FIG. 3.

FIGS. 3 and 4: Modified circular electrode

FIG. 3 and 4 illustrate a second embodiment of a corona electrode 10 arranged inside a second urisheath 11. FIG. 4 shows the cross section along line IV-IV in FIG. 3.

The second corona electrode head 12 and the second PE disc 13 is in this embodiment placed closer to each other than in the first embodiment of the corona electrode 1. This provides a smaller, but more concentrated corona when the second corona electrode head is operated with the same parameters as the first corona electrode head 2.

By performing corona treatment as illustrated in FIG. 1-4 and described earlier the urisheath can advantageously be treated after production. This advantageously allows for example adhesive to be applied to a urisheath irregardless of the method whereby the urisheath has been produced.

This allows the urisheath to be blow-molded, which, for example, allows the formation of ribs formed on the urisheath. Such ribs would, for example, not be possible to form on a urisheath during dip-molding.

Figure 7:
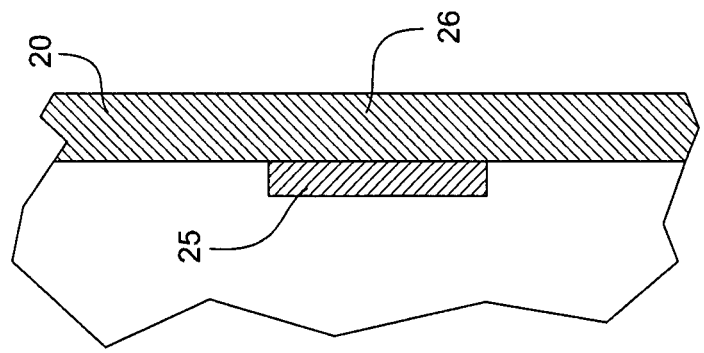
FIG. 7 is a cross-sectional view of a third embodiment of the inner encircling band and the outer encircling band associated with the tubular sheath.
Figure 6:
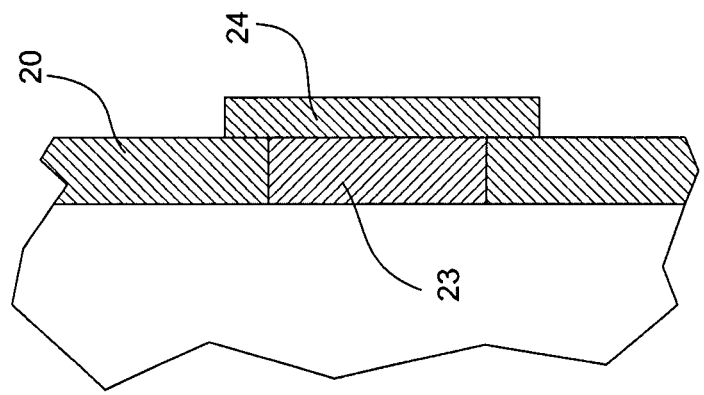
FIG. 6 is a cross-sectional view of a second embodiment of the inner encircling band and the outer encircling band associated with the tubular sheath.
Figure 5:
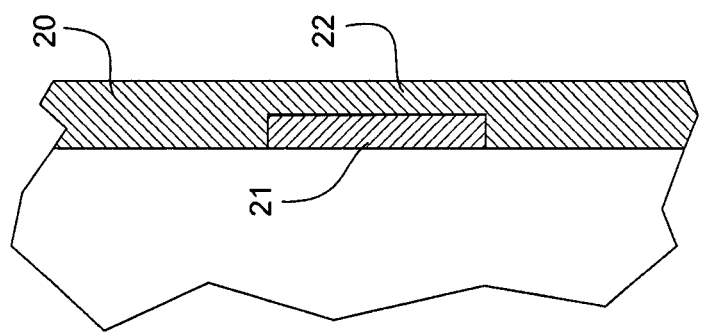
FIG. 5 is a cross-sectional view of a first embodiment of an inner encircling band and an outer encircling band associated with a tubular sheath.

FIGS. 5, 6 and 7: Oxidized Bands

FIGS. 5-7 show, seen in cross section, different embodiments on how the inner encircling band and the outer encircling band can be provided on the tubular sheath.

FIG. 5 shows a section of the wall 20 of the tubular sheath. In this embodiment the inner encircling band 21 is formed partly into the wall 20 of the tubular sheath. This can for example be by corona treatment, which has been applied to the tubular sheath for a limited time. The outer encircling band 22 is thus provided as the part of the tubular wall, which covers the inner encircling band and has not been exposed to corona treatment.

FIG. 6 shows a section of the wall 20 of the tubular sheath where the inner encircling band 23 has been formed as a through going part of the wall 20 of the tubular sheath. The outer encircling band 24 is applied subsequently, covering the inner encircling band. The outer encircling band is formed of the same material as the wall 20 of the tubular sheath.

In FIG. 7 the inner encircling band is applied as an extra layer to the inside of the urisheath. This can be done by for example applying an encircling silicone layer on a mandrel. The layer is oxidized where after the urisheath is rolled over the mandrel and due to acrylic lock-up the layer is transferred to the urisheath providing an inner encircling band 25, where the outer encircling band 26 can be understood to be part of the tubular wall 20 which covers the inner encircling band.

The oxidized inner encircling band advantageously allows different materials to be attached/provided on the urisheath. An adhesive layer could for example be applied to the encircling inner band.

The process whereby an oxidized elastomer, such as the inner encircling band, is provided will be understood in the following examples.

EXAMPLES

Example 1A

Selective Corona Discharge

Raw urisheaths were obtained in silicone elastomer Dow Corning C6-540. Then heat-treated for 5 min at 200° C. in order to evaporate low molecular uncured silicone.

The inside of a 30 mm diameter urisheath were corona treated with a circular electrode with a Voltage of 40,000V and a power of 120 W. The 24 mm diameter electrode was moved from one end to the other end of the inside of the sheath part of the product over a distance of 80 mm in 2 seconds. A distance of 2 to 4 mm from electrode edge to the inside surface were secured mechanically by a thin polyethylene disc 28 mm in diameter (see FIG. 1).

In this manner only inside of urisheath were treated reflected in a surface tension of above 35 dyn/cm on the inside and surface tension below 28 dyn/cm on the outside. With a higher power of 150 W instead or with the electrode approaching or touching the inside, an unwanted raised surface tension was seen on the outside in spots or totally, thus harming the release properties wanted on the outside.

On top of an aluminum mandrel, coated with a suitable silicone release coating, was applied an acrylic pressure sensitive adhesive, in this case Gelva 2853 from UCB-Solutia. The adhesive was dried and cured 5 min in an oven at 200° C. (effective temperature 130° C.). After cooling to 50° C. the corona treated silicone raw urisheaths were rolled on the mandrels. They were immediately unrolled. The adhesive was thereby transferred from the mandrel to the inside of the urisheath.

After 24 h at 40° C. Peel values at room temperature were on the same level (7 N) as for the same adhesive used on natural latex urisheaths and there were no adhesive residue. Unrolling values were lower and more stable (2 N).

Example 1B

Selective Corona Discharge

Raw urisheaths were obtained in silicone elastomer Dow Corning C6-540. The inside of a 30 mm diameter urisheath were corona treated with a circular electrode with a Voltage of 40,000V and a power of 80 W. The 24 mm diameter electrode was moved from one end to the other end of the inside of the sheath part of the product over a distance of 80 mm with a speed of 1000 mm/sec. A distance of 2 to 4 mm from electrode edge to the inside surface were secured mechanically by a thin PE disc 28 mm in diameter (see FIG. 1). In this manner only the inside of urisheath were treated reflected in a surface tension of above 32 dyn/cm on the inside and surface tension below 28 dyn/cm on the outside. On top of an aluminum mandrel, coated with a suitable silicone release coating, was applied an acrylic pressure sensitive adhesive, in this case Gelva 2853 from UCB-Solutia. The adhesive was dried and cured 45 sec. in an infrared oven with heating elements at 480° C. giving an effective temperature of 110° C. After cooling to 50° C. the corona treated silicone raw urisheaths were rolled on the mandrels. They were immediately unrolled. The adhesive was thereby transferred from the mandrel to the inside of the urisheath. After 24 h at 23° C. Peel values at room temperature were on the same level (7 N) as for the same adhesive used on natural latex urisheaths and there were no adhesive residue. Unrolling values were lower and even more stable (<2 N).

Example 1C

Selective Corona Discharge With an Extra Release Layer

Corona treated urisheaths were made as in process described in example 1B. After the step of placing the urisheath on the to of the adhesive coated mandrel, an thin layer of a special addition cure release silicone were applied by a roller The silicone was cured for 90 sec. in an infrared oven with heating elements at 450° C. giving an effective temperature of 150° C. After cooling to below 50° C. the urisheath was rolled off the mandrel and the adhesive was thereby transferred from the mandrel to the inside of the urisheath. After 24 h at 23° C. Peel values at room temperature were on the same level (7 N) as for the same adhesive used on natural latex urisheaths and there were no adhesive residue. Unrolling values were even lower and more stable in accelerated ageing at 40° C. and 60° C. than in example 1B.

Example 1D

Selective Corona Discharge on Other Silicone Materials

Raw urisheaths were obtained in silicone elastomer Dow Corning C6-540, Dow Corning C-530, GE-Bayer LSR 4040 and Wacker 3003/40. Parts of the Urisheaths were after-cured 1 h at 200° C. The inside of a 30 mm diameter urisheath were corona treated with a circular electrode with a Voltage of 40,000V and a power of 90 W. The 24 mm diameter electrode was moved from one end to the other end of the inside of the sheath part of the product over a distance of 80 mm with a speed of 1000 mm/min. A distance of 2 to 4 mm from electrode edge to the inside surface were secured mechanically by a thin PE disc 28 mm in diameter (see FIG. 1). In this manner only the inside of urisheath were treated reflected in a surface tension of above 34 dyn/cm on the inside and surface tension below 28 dyn/cm on the outside. On top of an aluminum mandrel, coated with a suitable silicone release coating, was applied an acrylic pressure sensitive adhesive, in this case Gelva 2853 from UCB-Solutia. The adhesive was dried and cured 45 sec. in an infrared oven with heating elements at 470° C. giving an effective temperature of 110° C. After cooling to 50° C. the corona treated silicone raw urisheaths were rolled on the mandrels. They were additionally cured 90 sec. in an infrared oven with heating elements at 480° C. giving an effective temperature of 120° C. on the mandrels used. After cooling to below 50° C. the urisheath was rolled off the mandrel and the adhesive was thereby transferred from the mandrel to the inside of the urisheath. After ageing for 1 week at 60° C. only urisheaths made of Dow Corning C6-540 and not cured for 1 hour at 200° C. could be unrolled. All the other samples made with or without after-curing could not be unrolled. However all these materials will be suitable to use if an extra release coating is used as in example 1C.

Example 2

Selective Corona Discharge

Raw urisheaths and pre-treatment by evaporation and corona discharge were done in the same way as in Example 1. On top of an aluminum mandrel, coated with a suitable silicone release coating, was applied a pre-treated silicone raw urisheath. On top of the silicone sheath was applied an acrylic pressure sensitive adhesive, in this case Gelva 2853 from UCB-Solutia. The adhesive was dried and cured 5 min in an oven at 200° C. (effective temperature 130° C.). After cooling to room temperature the corona urisheaths were rolled off the mandrels. When unrolling the urisheath the adhesive were transferred securely to the inside of the urisheath. After 24 h at 40° C. products showed good peel values (5 N) and no adhesive residue. Unrolling values were low (2 N).

Example 3

Silicone Tie-Layer

Raw urisheaths were obtained in silicone elastomer Dow Corning C6-540. On top of an aluminum mandrel, coated with a PTFE coating with release properties towards PSA and silicone, was applied the acrylic adhesive Gelva 2853 from UCB-Solutia. The adhesive was dried and cured 2 min in an oven at 200° C. (effective temperature 80° C.). On top of this Dow Corning silicone C6-540 diluted with 70% heptane were applied and pre-cured for 2 min. at 200° C. (effective temperature 100° C.). On top of this the raw urisheath were applied. The mandrel was then heated to an effective temperature of 150° C. in 8 minutes to secure curing of the silicone tie-layer. After 24 h at 40° C. products showed good peel values (5 N) and no adhesive residue. Unrolling values were low (2 N).

Example 4

E-Beam Irradiation

Raw urisheaths were pre-treated by E-Beam irradiation 2×35Gy in bulk. No corona pre-treatment was used. After the step of placing the urisheath on the to of the adhesive coated mandrel, in this case Gelva 2853 from UCB-Solutia, a thin layer of a special addition cure release silicone were applied by a roller The silicone was cured for 90 sec. in an infrared oven with heating elements at 450° C. giving an effective temperature of 140° C. After cooling to below 50° C. the urisheath was rolled off the mandrel and the adhesive was thereby transferred from the mandrel to the inside of the urisheath.

After 72 h at 60° C. adhesive was securely attached to the inside of the urisheath, this was tested by the "pressing together test", which includes bringing adhesive surface in contact with adhesive surface by collapsing the urisheath by hand, and immediately after peeling the two sides from each other by hand. On the reference samples without E-beam pre-treatment the adhesive did not peel from the adhesive, but showed nearly total failure in adhesive-silicone interface from one side of the silicone urisheath. In normal use this would mean a much extended possibility for leakage, and for adhesive residue sitting on the human skin after removal of the product. The "pressing together test" has been performed with urisheaths from example 1, 2 and 3, showing that adhesive is securely attached, which means no adhesive peel from the silicone. In other words, the adhesive applied to the corona treated part of silicone sits better, than the adhesive adheres to itself, when pressed together. It is to be noted, that several different commercially available silicone urisheath made by dipping process, did not pass this test, but showed at least partly failure in adhesive-silicone interface.

Example 5

Acrylic Tape

Corona treated samples were made in same way as Example 1 and the corona treated part was cut out. 5 different commercially available acrylate tapes were laminated together with the corona treated side. Commercial names for the tapes were: "Tesa Window", "Tesa Multisurface", "Tesa Transparent Universal", "Tesa 3191", "Tesa 4049" and "Impega Invisible Tape". Peel values after 0.5 h at 23° C. and 0.5 h at 40° C. were tested. 180° Peel values at 5 to 11 N were measured, whereas peel values below 0.5 N were measured for the untreated side or for not corona treated samples. In several cases the tape failed in the adhesive-backing interface. This example shows that a great variety of different acrylate adhesives can be attached to an oxidative treated silicone material. It also shows a possibility to use an adhesive transferred from a double side medical acrylate tape for a urisheath pre-treated after the method as described here.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A method of applying a pressure sensitive skin adhesive material to a cured, external urinary silicone catheter comprising:
    (a) providing a cured, external urinary silicone catheter having an inner surface and an outer surface;
    (b) selectively applying an oxidative process to only the inner surface of the silicone catheter along an annular inner band of the silicone catheter to provide an annular inner band of oxidized silicone; and
    (c) applying the pressure sensitive skin adhesive material to a surface of the annular inner band of oxidized silicone by (i) rolling the catheter over a mandrel coated with the adhesive material and (ii) unrolling the catheter from the mandrel, so as to transfer the adhesive material from the mandrel to the annular inner band.

2. The method according to claim 1, wherein the oxidative process is selected from the group consisting of oxidative-heat treatment, UV light, E-beam, gamma-irradiation, and chemical oxidative treatment.

3. The method according to claim 2, wherein the oxidative-heat treatment is selected from the group consisting of corona treatment, plasma treatment, and flame treatment.

4. The method of claim 1, wherein the adhesive material is a polar adhesive material.

5. The method of claim 4, wherein the polar adhesive is based on acrylics, polyether, polyvinylether, polyurethane, or polyvinylpyrolidone.

6. The method of claim 1, wherein the adhesive material is an acrylic pressure sensitive adhesive.

7. The method of claim 1, wherein the silicone catheter is fully cured.

8. The method of claim 1, wherein the silicone catheter is partly cured.

9. The method according to claim 2, wherein the oxidative-heat treatment is applied selectively on selected parts of the silicone catheter.

10. The method of claim 9, wherein the oxidative-heat treatment is applied selectively on an inside of the silicone catheter.

11. The method according to claim 1, wherein the oxidative process is a corona treatment.

12. An external urinary catheter having a silicone material of construction, comprising:
    a body having a first open end and a second closed end. the body defining an inner surface, an outer surface, and a length. between the first and second ends, the inner surface including. at least an annular inner band of oxidized silicone extending along less than the entire length of the body and the outer surface including an outermost annular band of non-oxidized silicone that covers at least the annular inner band; and
    a pressure sensitive skin adhesive disposed on the annular inner band of oxidized silicone and configured as a rolled layer of the adhesive material transferred from an adhesive-coated mandrel.

13. A silicone urisheath having an outer surface and an inner surface, the silicone urisheath comprising:
    an annular inner band of oxidized silicone forming the inner surface of the urisheath;
    an outermost annular band of non-oxidized silicone that forms the outer surface of the silicone urisheath; and
    a pressure sensitive skin adhesive that is (i) disposed on the annular inner band of oxidized silicone and (ii) configured as a rolled layer of the adhesive transferred from an adhesive-coated mandrel.

14. The silicone urisheath according to claim 13, wherein the oxidative process is selected from the group consisting of oxidative-heat treatment, UV light, E-beam, gamma-irradiation, and chemical oxidative treatment.

15. The silicone urisheath according to claim 14, wherein the oxidative-heat treatment is selected from the group consisting of corona treatment, plasma treatment, and flame treatment.

16. The silicone urisheath according to claim 13, wherein the adhesive material is a polar adhesive material.

17. The silicone urisheath according to claim 16, wherein the polar adhesive is based on acrylics, polyether, polyvinylether, polyurethane, or polyvinylpyrolidone.

18. The silicone urisheath according to claim 13, wherein the adhesive material is an acrylic pressure sensitive adhesive.

19. The method of claim 1, wherein selectively applying an oxidative process to only the inner surface of the silicone catheter includes selectively applying the oxidative process with a circular surface of an electrode.

20. The method of claim 1, wherein a circular electrode is inserted within the silicone catheter during application of the oxidative process.

\* \* \* \* \*